United States Patent [19]

Noebel et al.

[11] Patent Number: 5,204,088

[45] Date of Patent: Apr. 20, 1993

[54] HYDROPHOBIC SILICA COATING

[75] Inventors: Roger D. Noebel, Irvine; Lane Elliott, Laguna Hills, both of Calif.

[73] Assignee: Globe Technology Corporation, Irvine, Calif.

[21] Appl. No.: 749,486

[22] Filed: Aug. 15, 1991

Related U.S. Application Data

[63] Continuation of Ser. No. 423,084, Oct. 18, 1989, abandoned, which is a continuation of Ser. No. 339,775, Apr. 18, 1989, abandoned.

[51] Int. Cl.$^5$ ............................ A61K 7/32; A61K 9/12
[52] U.S. Cl. ........................................ 424/47; 424/401
[58] Field of Search ...................... 222/4; 424/47, 401

[56] References Cited

U.S. PATENT DOCUMENTS

| | | | |
|---|---|---|---|
| 3,207,386 | 9/1965 | Presant et al. | 424/47 |
| 4,071,374 | 1/1978 | Minton | 106/189 |
| 4,263,274 | 4/1981 | Kulkarni et al. | 424/47 |
| 4,278,655 | 7/1981 | Elmi | 424/47 |
| 4,411,883 | 10/1983 | Kenkare et al. | 424/47 |
| 4,680,173 | 7/1987 | Burger | 424/47 |
| 4,743,440 | 5/1988 | Callingham et al. | 424/47 |
| 4,889,711 | 12/1989 | Kai et al. | 424/47 |
| 4,935,224 | 6/1990 | Russo et al. | 424/47 |

*Primary Examiner*—Michael G. Wityshyn
*Attorney, Agent, or Firm*—Lyon & Lyon

[57] ABSTRACT

An applicator which can readily and conveniently generate an aerosol of hydrophobic silica particles without the need for hoppers, rotating vanes, compressed dry air purged rotors, venturis, or other complex apparatus, and a method of applying a friction enhancing and water repelling coating to a surface using such an applicator. The applicator can readily produce a submicron hydrophobic silica aerosol even from hydrophobic silica particles which normally aggregate into conglomerates of greater than $1\mu$ in diameter. The applicator uses an aerosol dispenser with a nozzle communicating with the interior of the container thereof, and a pressurized propellant. The dispenser is charged with a suspension of hydrophobic silica particles in a volatile liquid, for example ethanol. The applicator and method are particularly useful in applying a grip enhancing and water repelling coating to an individual's hands and/or various equipment, such as athletic equipment, prior to participating in sports where improved grip is desirable, such as in football, baseball, golf, etc. Further, high efficiency particulate filters can be readily and conveniently tested using the applicator.

1 Claim, No Drawings

HYDROPHOBIC SILICA COATING

CROSS-REFERENCE TO RELATED APPLICATION

This is a continuation of co-pending application Ser. No. 07/423,084, filed on Oct. 18, 1989, abandoned, which is a continuation of patent Ser. No., 339,775 filed Apr. 18, 1989 entitle Hydrophobic Silica Coating, now abandoned.

FIELD OF THE INVENTION

This invention relates to submicron hydrophobic silica particles, and in particular to a simple applicator which can readily generate an aerosol of submicron hydrophobic silica particles, even though the particles in the powder form which is used to prepare a suspension for charging the applicator, may be agglomerated into conglomerates of greater than 1μ. The resulting aerosol is useful to provide a water repellant and friction enhancing coating on a surface, or can be used to test high efficiency particulate air or gas filters.

TECHNOLOGY REVIEW

It has been previously recognized that it would be desirable in many situations, to provide a friction enhancing or water repellant coating on a surface. For example, it has been previously recognized that, in general, enhancing an individual's grip (which is dependent upon friction) would improve their performance in many sports. Such sports include ball handling sports (e.g., basketball, football), racquet sports (tennis, racquetball, squash) or other sports where the grip of an instrument is required. One known technique of enhancing grip is by the application of adhesive or tacky compositions to the hands. While such compositions can enhance grip, they are typically messy and inconvenient to use, and in addition do not provide a quick, clean, release from the surface. Thus, such adhesive or tacky compositions would, for example, be unsuitable for enhancing grip in ball handling sports. It is also well known to use talcs and various other powders to enhance an individual's grip in various sports. Many of those powders, though, typically rub off easily and thus must be frequently reapplied. In addition, many such powders are, at best, only poorly water repellent, and are easily washed off when exposed to moisture from either perspiration or contact with water.

It has also been previously known to generate an aerosol of submicron hydrophobic silica particles for use in testing high efficiency particulate air filters ("HEPA" filters). This was accomplished by using a dry hydrophobic silica powder composed of particles which, in their normal form, are agglomerated into larger diameter 'particles' (referred to herein as "conglomerates"). To disaggregate such conglomerates and generate the aerosol, the dry silica powder was charged into a hopper of an aerosolizing generator, and mixed with dry air or nitrogen therein while being stirred by rotating vanes. The resulting air/powder mixture was transferred into a compressed air purged rotor which then delivered the mixture to an air pressure driven venturi and hence out of the aerosolizing generator. Such an aerosolizing generator, which generates an aerosol of particles from a dry powder only, is relatively complex, expensive, bulky, and required an external source of dry compressed air or nitrogen, and electricity.

SUMMARY OF THE INVENTION

The present invention provides a means by which an aerosol of submicron hydrophobic silica particles can be conveniently and rapidly generated, even though the hydrophobic silica particles in the powdered form which is used to prepare a suspension for charging the applicator, may be aggregated into conglomerates of 1μ or larger. The resulting aerosol can be applied to a surface to provide a coating which has both water repelling and friction enhancing properties. For example, the resulting aerosol can be applied to an individual's hands to provide a coating which improves grip and does not come off readily even when exposed to moisture, from perspiration or contact with water, but which is readily removed by ordinary soap and water. The present invention produces the desired aerosol without any requirement for the relatively bulky, complex, and expensive equipment, previously used to disaggregate particles of dry hydrophobic silica powder. This is accomplished by means of an applicator of the present invention. The applicator comprises an aerosol dispenser, preferably of conventional construction (sometimes known as an "aerosol bomb"), which has a container, a pressurized propellant therein, and a nozzle communicating with the interior of the container. The foregoing aerosol dispenser is charged with a colloidal suspension of hydrophobic silica particles in a volatile liquid, such that said hydrophobic silica suspension can be ejected by said propellant through said nozzle as an aerosol.

The hydrophobic silica particles are preferably pyrogenic (i.e., "fumed") silica particles, which are normally hydrophilic but have been provided with a hydrophobic coating. Pyrogenic silica is silica which is prepared by high temperature hydrolysis of a halosilane, such as tetrachlorosilane, to produce silica particles having a mean diameter of less than one nanometer ("nm"). These particles can be provided with a hydrophobic coating, for example by treatment with an alkyl silane, such as a branch chain halosilane like tert-butyl silane, or with a long chain fatty acid silane such as stearyl silane. Another known method for providing a hydrophobic coating, is to coat the particles with a silicone. Such hydrophobic pyrogenic silica, with a silicone coating, is sold by Cabot Corporation (Tuscola, IL, U.S.A.) under the trademark CAB-O -SIL TS-720, and by Dugussa Corporation (Ridgefield Park, N.J., U.S.A.) under the trademark AEROSIL. Hydrophobic pyrogenic silica particles typically have a mean diameter of about 5–40 nm, and are normally aggregated into conglomerates of greater than about 1μ in diameter. It is believed that the turbulence created in the nozzle during ejection of the aerosol therethrough, results in the disaggregation of the conglomerates. Thus, the nozzle selected is preferably one which will produce an aerosol with the smallest mean diameter particles, in sufficient quantity, and without clogging. Furthermore, the presence of the liquid may promote disaggregation.

When it is desired to apply a water repelling or friction enhancing coating to a surface, such as the palms of an individuals hands, the hydrophobic silica aerosol generated by the applicator described above is simply directed toward the surface upon which the coating is desired.

DETAILED DESCRIPTION OF THE EMBODIMENTS OF THE INVENTION

The present invention provides for the application of a submicron hydrophobic silica particle coating, by using a suspension of such particles in a volatile solvent in an aerosol dispenser. By such means, a coating of submicron particles can be produced even though the hydrophobic silica particles in the powder form, are typically aggregated into much larger conglomerates. Such dispensers themselves are very well known conventional aerosol dispensers or "bombs", which are widely used in both industry and households for dispensing liquids such as hairsprays, paints, deodorizers, cleansers, and many other products. Such aerosol dispensers typically consist essentially of a container in the form of a cylindrical can, with a nozzle positioned on top which in turn communicates through a valve and tube with the can's interior. The liquid to be dispensed is placed within the can along with a pressurized propellant gas, such that depressing the nozzle causes the valve to be opened and the liquid to be urged from the can under pressure of the propellant, and through the nozzle in the form of an aerosol.

In the present case though,. the dispenser is filled with a colloidal suspension of hydrophobic silica particles in a suitable volatile liquid. The presently prefered hydrophobic pyrogenic silica is in the form of a powder sold under the trademark CAB-O-SIL TS-720, by Cabot Corporation, Tuscola, IL, U.S.A. The foregoing hydrophobic pyrogenic silica particles (which are normally hydrophilic) are coated with a silicone. The resulting hydrophobic particles have a mean diameter of between about 7 to 20 nm, but in the powdered form a substantial proportion of them are aggregated into conglomerates. The choice of volatile liquid depends upon the end use contemplated. For most applications, this will mean that the liquid should be sufficiently volatile to evaporate rapidly at normal indoor or outdoor temperatures. In addition, the volatile liquid should not adversely affect the surface to which the aerosol is to be applied. Since it is desirable that the coating can be applied to human skin, it should not adversely affect the skin. For the foregoing reasons, an alcohol, such as one of the C1 to C4 alcohols, is used as the volatile liquid. The alcohol used is preferably ethanol.

A preferred suspension of hydrophobic pyrogenic silica for the foregoing purpose, is one consisting of 8% CAB-O-SIL TS-720 in anhydrous, denatured alcohol. The pressurized propellent can be any of well known propellants used in the spray bomb art, for example a mixture of 18.6% butane, 12.6% isobutane and 28.8% propane has been found acceptable (all percentages expressed in this application are weight percentages, unless otherwise indicated). Of course, the ethanol can be replaced by another volatile liquid particularly where the hydrophobic silica will not be applied to an individuals skin. For example, if the applicator is to be used to apply a water repellent coating to an inanimate article, the volatile liquid could be 1,1,1-trichloroethane.

A water repellent friction enhancing coating can be applied to a surface using the applicator described above, which is charged with the hydrophobic pyrogenic silica in alcohol suspension, described above. This is accomplished simply by pressing the nozzle of the applicator to open the valve thereof, and directing the resulting aerosol toward the surface. Preferably the applied coating is then rubbed in (e.g., by rubbing the hands together when the coating is applied to the hands). This rubbing in apparently helps to further disaggregate the particles, spread the coating more evenly, and reduces the chances that it will come off on another surface where it would be undesirable (e.g., on a football, or on a user's clothes). In the foregoing manner, such a coating was applied to the palms of an individuals hands. An increased friction between the palms and the surface of a wooden object was immediately noted when the object was gripped following the application of the hydrophobic silica coating from the aerosol.

In the same manner, the applicator charged with the same hydrophobic pyrogenic silica suspension, was used to apply a coating to the palms of an individuals hands, prior to gripping a golf club. A greater grip was immediately apparent which persisted throughout several hours of a golf game. Following this, the hands were dipped in water and it was noted that the water tended to bead on the palms (indicating a water repellant coating thereon) and that there was no loss in enhanced gripping when the club was again gripped. The foregoing experiment was repeated in cold weather (down to 40° F.) and in warmer (into the 80° F. range) and humid weather. Furthermore, the hands remained dry even under conditions when they would have been expected to perspire had they not been coated with the hydrophobic silica. Similarly, a coating of hydrophobic silica was applied using the applicator as described, to a golf club handle. The handle, prior to applying the coating, normally became wet when dipped in water. However, following application of the coating, the handle was then dipped in water and removed, and was observed to remain dry. Thus, the applicator had applied a highly water repellent coating of hydrophobic silica to the handle. It was also found that the hydrophobic silica coating so applied, although apparently not affected by direct exposure to water, could be readily removed simply by washing with ordinary soap and water.

The applicator of the present invention, which includes the hydrophobic silica suspension, can also be used to test the integrity of a HEPA filter. Such a filter and a method of testing it , is described in U.S. Pat. No. 4,213,768 to Bauman et al. In the present case the method of testing the HEPA filter was essentially the same as described in the Bauman et al patent. In the present case though, an aerosol of hydrophobic silica particles was conveniently generated by the applicator of the present invention, from a hydrophobic silica/volatile liquid suspension therein. In the present trial, an applicator of the present invention was used which had a 6% by weight suspension of the hydrophobic silica particles sold under the CAB-O-SIL TS-720 trademark, as described above, in a 1, 1, 1-trichloroethane solvent. The propellant was chlorodifloromethane. Otherwise the testing procedure was the same as described in Bauman et al. It was found that the foregoing method, using the aerosol generated by the present applicator with hydrophobic silica particles/volatile liquid suspension, also successfully identified the presence of a pinhole (estimated diameter 0.2 mm) in the filter, as did the method described in Bauman et al, but without the use of the bulky apparatus of Bauman et al, with its hopper, rotating vanes, compressed air purged rotor, venturi, and external compressed dry air or nitrogen source and electricity source.

It will be appreciated that alterations to the embodiments described above are of course possible. For example, other suitable volatile liquids could be used in place of the alcohol or trichloroethane depending upon the particular surface to which the coating is to be applied. It is necessary though that the liquid be such that the hydrophobic silica will form a suspension therein. Thus, if the hydrophobic silica merely floated on the surface of the liquid, this would be unsuitable. Thus water would not be suitable since the hydrophobic silica does not form a suspension in it, but rather floats on the surface of the water. It will also be appreciated that the applicator can be used to conveniently apply a friction enhancing or water repelling coating to many other surfaces other than those specifically described. For example, it may be desirable to use the applicator to apply such a coating to the soles of the feet in surfing. In addition, it may be desirable to apply the coating to the entire hands, as in the case where it is necessary to retain a pair of heavy gloves (e.g., hockey gloves) in place or to apply the coating for sports other than ball or instrument handling sports (e.g., for mountain climbing or wrestling).

Further modifications and alterations to the present invention are additionally possible, and the invention is not limited to those embodiments described in detail above.

We claim:

1. A system for at least one of repelling water and enhancing friction on a surface comprising, an applicator comprising an aerosol dispenser, wherein the aerosol dispenser includes a container, a pressurized propellant therein, and a nozzle communicating with the interior of the container, and a colloidal suspension of hydrophobic silica particles within the container consisting of hydrophobic silica particles suspended in a C1 to C4 alcohol, wherein the hydrophobic silica particles have a mean diameter of between about 5 to 40 nm, a substantial proportion of which particles are aggregated into conglomerates of greater than about 1μ in diameter, and which particles have been rendered hydrophobic by treatment with an organosilane having hydrocarbon chains of between 4 to 30 carbon atoms, said suspension being ejectable by said propellant through said nozzle as an aerosol to a surface to provide a coating of silica particles agglomerated into conglomerates of submicron sizes.

* * * * *